(12) United States Patent
Yanagisawa et al.

(10) Patent No.: US 7,655,450 B2
(45) Date of Patent: Feb. 2, 2010

(54) POLYPEPTIDE HAVING AMIDASE ACTIVITY AND GENE THEREOF

(75) Inventors: Satohiro Yanagisawa, Hyogo (JP); Makoto Ueda, Hyogo (JP); Hirokazu Nanba, Hyogo (JP)

(73) Assignee: Kaneka Corporation, Osaka (JP)

( * ) Notice: Subject to any disclaimer, the term of this patent is extended or adjusted under 35 U.S.C. 154(b) by 578 days.

(21) Appl. No.: 10/587,085

(22) PCT Filed: Jan. 26, 2005

(86) PCT No.: PCT/JP2005/000951

§ 371 (c)(1),
(2), (4) Date: Jul. 21, 2006

(87) PCT Pub. No.: WO2005/075650

PCT Pub. Date: Aug. 18, 2005

(65) Prior Publication Data

US 2009/0136994 A1     May 28, 2009

(30) Foreign Application Priority Data

Feb. 4, 2004   (JP) .............................. 2004-028041

(51) Int. Cl.
C12N 9/78    (2006.01)
C07H 21/04   (2006.01)
C12N 15/63   (2006.01)
C12N 1/20    (2006.01)
C12P 21/00   (2006.01)

(52) U.S. Cl. .............. 435/227; 536/23.1; 536/23.2; 435/252.33; 435/71.1; 435/320.1

(58) Field of Classification Search ................ None
See application file for complete search history.

(56) References Cited

U.S. PATENT DOCUMENTS

| 5,130,240 A | 7/1992 | Ozaki et al. |
| 5,252,470 A | 10/1993 | Ozaki et al. |
| 2004/0023257 A1* | 2/2004 | Barton et al. .................. 435/6 |

FOREIGN PATENT DOCUMENTS

| CA | 1336414 | 7/1995 |
| EP | 0 334 358 | 9/1989 |
| JP | 63-87998 | 4/1988 |
| JP | H7-106149 B2 | 9/1989 |
| JP | 2-234678 | 9/1990 |
| JP | 2843596 | 1/1999 |
| JP | 2002-253256 | 9/2002 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Barton et al, US20040023257, Filing Date: Jan. 20, 2003 Seq ID No. 113&114. Alignment with Seq ID No. 1 & 3.*
Takegawa et al, Cloning, sequencing, and expression of Arthrobacter protophormiae endo-beta-N-acetylglucosaminidase in *Escherichia coli*. Arch Biochem Biophys. Feb 1, 1997;338(1):22-8.*
Ozaki, A. et al., "A D-Amidase Constitutive Mutant from *Arthrobacter* sp. NJ-26," Bioscience Biotechnology Biochemistry, vol. 57, No. 3, 1993, pp. 520-521.
International Preliminary Report on Patentability (Chapter I of the Patent Cooperation Treaty) from Corresponding International Application No. PCT/JP2005/000951, dated Sep. 19, 2006, 7 pages.
Y. Asano, et al., "Purification and Characterization of Amidase which Participates in Nitrile Degradation," *Agric. Biol. Chem.*, 46(5), 1175-81 (1982).
D.H. Baek, "Characterization of a Thermostable D-Stereospecific Alanine Amidase from *Brevibacillus borstelensis* BCS-1," *Appl. Environ. Microbiol.*, 69(2) 980-86 (2003).
H. Komeda et al., "Gene Cloning, Nucleotide Sequencing, and Purification and Characterization of the D-Stereospecific Amino-acid Amidase from *Ochrobactrum anthropi* SV3," *Eur. J. Biochem.*, 267(7), 2028-35 (2000).
A. Ozaki, et al., "Enzymatic Production of D-Alanine from DL-Alaninamide by Novel D-Alaninamide Specific Amide Hydrolase," *Biosci. Biotech. Biochem.*, 56(12), 1980-84 (1992).

* cited by examiner

*Primary Examiner*—Sheridan Swope
(74) *Attorney, Agent, or Firm*—Hamre, Schumann, Mueller & Larson, P.C.

(57) ABSTRACT

It is an object of the present invention to provide a novel amidase that is useful for production of an optically active amino acid, and in particular, a D-amino acid, and a production method thereof.

The present invention relates to a novel D-amidase isolated and purified from the *Arthrobacter* sp. KNK1101J, a gene encoding the above amidase, a recombinant plasmid comprising the above gene, and a transformant into which the above amidase gene has been introduced. In addition, the present invention also relates to a method for producing the amidase, comprising culturing the *Arthrobacter* sp. KNK1101J or the above transformant, and collecting the above amidase.

17 Claims, 1 Drawing Sheet

POLYPEPTIDE HAVING AMIDASE ACTIVITY AND GENE THEREOF

RELATED APPLICATIONS

This application is §371 filing based on PCT/JP2005/000951, filed Jan. 26, 2005, and claims priority to the Japanese Patent Application No. 2004-028041, filed Feb. 4, 2004. The disclosure of each of these applications is incorporated by reference herein in its entirety.

BACKGROUND

1. Technical Field

The present invention relates to a polypeptide having amidase activity, a gene thereof, a microorganism or a transformant that is able to produce the above polypeptide thereof, and a method for producing amidase using the above microorganism or the transformant thereof.

2. Background Art

Amidase (enzyme No. [EC3.5.1.4]) is an enzyme, which hydrolyzes a carboxylic amide to carboxylic acid and ammonia. It has been known that this enzyme has industrially useful activities. For example, this enzyme stereoselectively hydrolyzes a racemic α-amino acid amide to generate an optically active α-amino acid. Such an optically active α-amino acid is a compound that is useful as a synthetic intermediate of pharmaceuticals or a sweetener. It has also been reported that amidase catalyzes hydrolysis of an ester as a substrate (Non-Patent Document 1).

A large number of methods for producing optically active α-amino acids have been known. However, the mass production of D-α-amino acids via a fermentation method has been considered particularly difficult. Thus, it has been desired that an inexpensive efficient synthetic method be developed. For example, as a method for synthesizing D-α-amino acid via biological means, the following synthetic methods, which involve the use of a microorganism or an enzyme having amidase activity and optical resolution of a racemic α-amino acid amide, have been known.

(1) A method for producing a D-α-amino acid from a racemic α-amino acid amide, using activity for specifically hydrolyzing the D-α-amino acid amide of a microorganism belonging to genus *Rhodococcus* (Patent Document 1).

(2) A method for producing a D-α-amino acid from a racemic α-amino acid amide, using aminopeptidase produced by a microorganism belonging to genus *Achromobacter, Corynebacterium, Flavobacterium, Bacillus, Micrococcus, Cellulomonas, Pseudomonas, Protaminobacter, Mycobacterium, Arthrobacter*, or *Streptomyces* (Patent Document 2).

(3) A method for producing D-alanine from a racemic alanine amide, using amidase produced by a microorganism belonging to genus *Arthrobacter* (Patent Documents 3 and 4).

(4) A method for producing a D-α-amino acid from a racemic α-amino acid amide, using activity for specifically hydrolyzing the D-α-amino acid amide of a microorganism belonging to genus *Achromobacter* (Patent Document 5).

(5) A method for producing a D-α-amino acid from a racemic α-amino acid amide, using a transformant having a D-amino acid amidase gene derived from a microorganism, which has been modified by genetic engineering (Patent Document 6).

However, in the case of the methods described in (1) to (4) above, since the hydrolytic activity of the microorganisms used is low, it cannot be said that these methods are satisfactory for industrial applications.

In addition, in the case of the method described in (5) above, only D-amino acid amidase derived from bacteria belonging to genus *Ochrobactrum* is described, and bacteria belonging to genus *Arthrobacter* are not described at all.

It has been generally known that bacteria belonging to genus *Arthrobacter* produce amidase. The enzyme has been purified and isolated, and the properties thereof have been then clarified (Patent Documents 3 and 4 and Non-Patent Documents 2 and 3). However, the amino acid sequence of the above enzyme and the nucleotide sequence of a gene encoding the above enzyme have not yet been reported.

[Patent Document 1] Japanese Patent Laid-Open No. 63-87998

[Patent Document 2] Japanese Patent Publication No. 7-106149

[Patent Document 3] U.S. Pat. No. 5,130,240

[Patent Document 4] U.S. Pat. No. 5,252,470

[Patent Document 5] Japanese Patent Laid-Open No. 2-234678

[Patent Document 6] Japanese Patent Laid-Open No. 2002-253256

[Non-Patent Document 1] Eur. J. Biochem., 2000, Vol. 267, p. 2028

[Non-Patent Document 2] Bioscience, Biotechnology and Biochemistry, 1992, Vol. 56, No. 12, p. 1980

[Non-Patent Document 3] Agricultural and Biological Chemistry, 1982, Vol. 46, No. 5, p. 1175

SUMMARY

Disclosure of the Invention

Problems to be Solved by the Invention

Taking into consideration the aforementioned circumstances, it is an object of the present invention to provide a novel D-amidase, which can be used for the optical resolution of a racemic amino acid amide and a racemic amino acid ester. It is another object of the present invention to determine the amino acid sequence of the above D-amidase and the nucleotide sequence of the gene thereof to provide a microorganism or a transformant that is able to produce the above enzyme, and a method for producing the above enzyme using them.

Means for Solving the Problems

As a result of intensive studies directed towards achieving the aforementioned objects, the present inventors have separated from the soil, bacteria belonging to genus *Arthrobacter*, which produce a novel D-amidase that stereoselectively hydrolyzes a D-amino acid amide and a D-amino acid ester. Thereafter, the inventors have isolated and purified the above amidase from the above bacteria, so that they have achieved isolation of an amidase gene and its expression in host microorganisms, thereby completing the present invention.

That is to say, the present invention relates to a polypeptide described in the following (a) or (b):

(a) a polypeptide, which has the amino acid sequence shown in SEQ ID NO: 1 of the sequence listing; or (b) a polypeptide, which has an amino acid sequence formed by comprising a substitution, insertion, deletion, and/or addition of one or more amino acids in the amino acid sequence shown in SEQ ID NO: 1 of the sequence listing, and which has amidase activity.

The present invention also relates to DNA encoding the above polypeptide.

The present invention also relates to DNA described in any one of the following (c) to (e):

(c) DNA, which has the nucleotide sequence shown in SEQ ID NO: 3 of the sequence listing;

(d) DNA, which hybridizes with DNA having a nucleotide sequence that is complementary to the nucleotide sequence shown in SEQ ID NO: 3 of the sequence listing under stringent conditions, and which encodes a polypeptide having amidase activity; and (e) DNA, which has a nucleotide sequence resulting from substitution, insertion, deletion, and/or addition of one or more nucleotides in the nucleotide sequence shown in SEQ ID NO: 3 of the sequence listing, and which encodes a polypeptide having amidase activity.

In addition, the present invention relates to a recombinant plasmid, which is obtained by insertion of the above DNA into a vector.

Moreover, the present invention relates to a transformant, which is obtained by transformation of a host microorganism with the above DNA or recombinant plasmid.

Furthermore, the present invention relates to a microorganism, which is able to produce the above polypeptide and belongs to genus *Arthrobacter*.

Still further, the present invention relates to a method for producing amidase, which comprises culturing the above microorganism or the above transformant that is able to produce a polypeptide, accumulating the above polypeptide in the culture, and collecting the above polypeptide.

ADVANTAGES OF THE INVENTION

The present invention comprises the aforementioned structures and enables efficient production of novel amidase. In addition, the present invention enables efficient production of D-amino acid from an amino acid amide or an amino acid ester, using the above amidase, or microorganisms that produce the above amidase.

DETAILED DESCRIPTION OF THE DRAWINGS AND THE PRESENTLY PREFERRED EMBODIMENTS

Best Mode for Carrying Out the Invention

The present invention will be described in detail below.

First, the polypeptide of the present invention will be described. The polypeptide of the present invention is a polypeptide, which has amidase activity and enables the stereoselective hydrolysis of a D-amino acid amide and a D-amino acid ester.

In the present invention, the amidase activity of the polypeptide can be detected and measured by carrying out a reaction at 30° C. in a tris (hydroxymethyl)aminomethane (Tris)-HCl buffer solution (pH 8.5) that contains a 50 mM D-phenylalanine amide, and then quantifying the generated phenylalanine by high performance liquid chromatography (HPLC) or the like.

The polypeptide of the present invention can be obtained from a microorganism having amidase activity. The type of such a microorganism is not particularly limited, as long as it produces the above polypeptide. Examples of such a microorganism include microorganisms belonging to genus *Arthrobacter*. Among others, *Arthrobacter* sp. are preferable, and *Arthrobacter* sp. KNK1101J, which has been newly isolated from the soil by the present inventors, is more preferable.

The aforementioned *Arthrobacter* sp. KNK1101J has been deposited with the National Institute of Advanced Industrial Science and Technology, an Independent Administrative Institution under the Ministry of Economy, Trade and Industry, at the AIST (Tsukuba Central 6, Higashi 1-1-1, Tsukuba, Ibaraki, Japan) (accession No. FERM BP-10192: a national deposition on Oct. 22, 2003 has been transferred to an international deposition under the provisions of the Budapest Treaty).

The mycological properties of the *Arthrobacter* sp. KNK1101J will be described below.

1. Form

1) *Bacillus* having a diameter of approximately 0.7 to 0.8 μm and a length of approximately 1.0 to 1.5 μm 2) Gram staining: positive 3) Motility: no 4) Sporulation: no 5) Cell polymorphism: no 6) Colony form on broth agar plate medium: round shape, smooth entire fringe, low convex, lustrous, and light yellow color 2. Cultural Properties 1) Nutrient agar (manufactured by Oxoid) medium
   Color: no; luster: no; pigment production: no 2) Nutrient broth (manufactured by Oxoid) medium
   Surface growth: no; turbidity of medium: yes 3) Gelatin stab culture
   Growth: no; gelatin change: no 4) Litmus milk
 Coagulation: no; liquefaction: no 3. Physiological Test 1) Nitrate reduction: −

2) Denitrification reaction: −

3) MR test: −

4) VP test: −

5) Indole generation: −

6) Hydrogen sulfide generation: −

7) Hydrolysis of starch: +

8) Use of citric acid Koser: +; Christensen: +

9) Use of inorganic nitrogen Nitrate: +; ammonium salt: +

10) Urease activity: −

11) Oxidase activity: −

12) Catalase activity: +

13) β-galactosidase activity: +

14) Arginine dihydrolase activity: −

15) Lysine decarboxylase activity: −

16) Tryptophan deaminase activity: −

17) Gelatinase activity: −

18) Pyrazinamidase activity: +

19) Pyrrolidonyl allyl amidase activity: +

20) Alkaline phosphatase activity: +

21) β-glucuronidase activity: −

22) N-acetyl-β-glucosaminidase activity: −

23) α-glucosidase activity: +

24) Esculin (β-glucosidase) activity: +

25) Gelatin hydrolytic activity: −

26) Growth range
 pH 5: +; pH 9: +; pH 10: +
 20° C.: +; 25° C.: +; 40° C.: +W; 45° C.: −

27) Growth conditions
 Aerobic: +; Anaerobic: −

28) O-F test (oxidation/fermentation): −/−

29) Generation of acid and gas from sugars (acid/gas)
 L-arabinose: −/−
 D-glucose: +/−
 D-fructose: +/−
 Maltose: −/−
 Lactose: −/−
 D-sorbitol: −/−
 Inositol: −/−
 D-xylose: +/−
 D-mannose: +/−
 D-galactose: +/−
 Sucrose: +/−
 Trehalose: +W/−
 D-mannitol: +/−
 Glycerin: +/−

30) Fermentation test
 Glucose: −
 Ribose: −
 Xylose: −
 Mannitol: −
 Maltose: −
 Lactose: −
 Saccharose: −
 Glycogen: −

31) Main menaquinone component: MK-9 ($H_2$)

32) Fatty acid composition in cell mass

TABLE 1

| fatty acid | | component ratio (%) |
|---|---|---|
| C15:0 | ANTEISO | 60.58 |
| C15:0 | ISO | 11.44 |
| C16:0 | ISO | 10.63 |
| C17:0 | ANTEISO | 7.06 |
| C16:0 | | 4.14 |
| C14:0 | ISO | 3.13 |
| C14:0 | | 1.88 |
| C17:0 | | 1.14 |

The microorganism that produces the polypeptide of the present invention may be either the wild strain of the aforementioned microorganism, or a mutant strain obtained by mutation and improvement. Such a mutant strain can be obtained by methods known to persons skilled in the art, such as UV irradiation or treatment with agents such as N-methyl-N'-nitro-N-nitrosoguanidine (NTG) or ethyl methanesulfonate (EMS).

The type of a medium used to culture the microorganism that produces the polypeptide of the present invention is not particularly limited, as long as the above microorganism can grow therein. Ordinary liquid mediums that contain the following nutrients can be used. That is, examples of a carbon source may include: carbohydrates such as glucose or sucrose; alcohols such as ethanol or glycerol; fatty acids such as oleic acid or stearic acid and the esters thereof; and oils such as rapeseed oil or soybean oil. Examples of a nitrogen source may include ammonium sulfate, sodium nitrate, peptone, casamino acid, corn steep liquor, bran, and yeast extract. Examples of inorganic salts may include magnesium sulfate, sodium chloride, calcium carbonate, dipotassium hydrogen phosphate, and potassium dihydrogen phosphate. Examples of other suitable nutrients may include malt extract and meat extract.

Moreover, small quantities of substances for enhancing the production of amidase, which include amides such as an amino acid amide or a fatty acid amide, or esters such as an amino acid ester or a fatty acid ester, can also be added. The concentration of such an amidase production-enhancing substance contained in a medium is between 0.001% by weight and 10% by weight, and preferably between 0.01% by weight and 1% by weight.

The culture can be aerobically carried out within a temperature range between 10° C. and 60° C., and preferably between 20° C. and 50° C., and a pH range between pH 3 and 11, and preferably between pH 5 and 9. The culture period is between approximately 1 and 5 days. In addition, either a batch culture method or a continuous culture method may be applied.

After completion of the culture, the cells are harvested from the culture broth by centrifugation or the like, and the harvested cells are then disrupted by means such as ultrasonic disruption to obtain a crude enzyme solution. Thereafter, this crude enzyme solution is purified by salting-out, column chromatography, or the like to obtain the polypeptide of the present invention.

As stated above, the polypeptide of the present invention may be either a natural enzyme obtained from microorganisms, or a recombinant enzyme produced utilizing genetic recombination technology. An example of such a natural enzyme is a polypeptide having the amino acid sequence shown in SEQ ID NO: 1 of the sequence listing.

In addition, the polypeptide of the present invention may also be a polypeptide, which has an amino acid sequence resulting from substitution, insertion, deletion, and/or addition of one or more amino acids in the amino acid sequence shown in SEQ ID NO: 1 of the sequence listing, and which has amidase activity.

An "amino acid sequence resulting from deletion, addition, insertion, and/or substitution of one or more amino acids" can be obtained by deleting, adding, inserting, and/or substituting amino acid(s) according to methods known to persons skilled in the art, such as a site-directed mutagenesis. Specifically, such methods are described in publications such as Nucleic Acid Res. 10, 6487 (1982), and Methods in Enzymology 100, 448 (1983).

Moreover, the term "polypeptide, which has amidase activity" is used to mean a polypeptide exhibiting 10% or more of the amidase activity of a polypeptide having the amino acid sequence shown in SEQ ID NO: 1, when measured under the aforementioned activity measurement conditions, preferably 40% or more, more preferably 60% or more, and further more preferably 80% or more.

Next, the DNA of the present invention will be described. The DNA of the present invention may be DNA encoding the aforementioned polypeptide. An example is DNA having the nucleotide sequence shown in SEQ ID NO: 3 of the sequence listing.

In addition, the DNA of the present invention may also be either DNA hybridizing with DNA having a nucleotide sequence complementary to the nucleotide sequence shown in SEQ ID NO: 3 of the sequence listing under stringent conditions, or DNA having a nucleotide sequence resulting from substitution, insertion, deletion, and/or addition of one or more nucleotides in the nucleotide sequence shown in SEQ ID NO: 3. Any type of DNA is included in the DNA of the present invention, as long as it encodes the aforementioned polypeptide having amidase activity.

The expression "DNA hybridizing with DNA having a nucleotide sequence complementary to the nucleotide sequence shown in SEQ ID NO: 3 of the sequence listing under stringent conditions" is used herein to mean DNA capable of specifically forming a hybrid with DNA having nucleotide sequence complementary to the nucleotide sequence shown in SEQ ID NO: 3 of the sequence listing, when the colony hybridization method, the plaque hybridization method, the Southern hybridization method, or the like is carried out.

The term "stringent conditions" is used herein to mean conditions wherein hybridization is carried out at 65° C. in an aqueous solution consisting of 75 mM trisodium citrate, 750 mM sodium chloride, 0.5% sodium dodecyl sulfate, 0.1% bovine serum albumin, 0.1% polyvinylpyrrolidone, and 0.1% Ficoll 400 (manufactured by Amersham Biosciences), and wherein washing is then carried out at 60° C. with an aqueous solution consisting of 15 mM trisodium citrate, 150 mM sodium chloride, and 0.1% sodium dodecyl sulfate, for example. Such stringent conditions are preferably conditions wherein after hybridization has been carried out under the aforementioned conditions, washing is carried out at 65° C. with an aqueous solution consisting of 15 mM trisodium citrate, 150 mM sodium chloride, and 0.1% sodium dodecyl sulfate. Such stringent conditions are more preferably conditions wherein after hybridization has been carried out under the aforementioned conditions, washing is carried out at 65° C. with an aqueous solution consisting of 1.5 mM trisodium citrate, 15 mM sodium chloride, and 0.1% sodium dodecyl sulfate.

Moreover, the term "nucleotide sequence resulting from deletion, addition, insertion, and/or substitution of one or more nucleotides" is used to mean a nucleotide sequence obtained by deletion, addition, insertion, and/or substitution of nucleotides, which can be deleted, added, inserted, and/or substituted by methods known to persons skilled in the art, which are described, for example, in *Tanpaku Kakusan Koso Zokan* (Proteins, Nucleic acids, and Enzymes, Supplement), *Idenshi Zofuku PCR Ho* (Gene Amplification PCR Method), 35 (17), 2951-3178 (1990), or PCR Technology (1990), edited by Henry A. Erlich, translated by Ikunoshin Kato.

The DNA of the present invention (amidase gene) can be obtained from the aforementioned microorganisms having amidase activity. For example, the following method can be applied to obtain DNA of interest.

First, the amino acid sequence of the N-terminus of amidase that has been purified from microorganisms having amidase activity is determined using a vapor-phase protein sequencer or the like. Further, protease such as lysyl endopeptidase is allowed to act on the purified amidase, so that the amidase can be digested into a polypeptide with a suitable size, and the obtained polypeptide is then purified by HPLC or the like to determine an internal amino acid sequence according to the aforementioned method. Based on the resultant N-terminal amino acid sequence and internal amino acid sequence, DNA primers are designed and synthesized.

Thereafter, chromosomal DNA is isolated from microorganisms used as origins of amidase. Such chromosomal DNA is obtained by dissolving the cultured cells in a surfactant, cetyltrimethylammonium bromide (CTAB), chloroform, phenol, or the like, treating the cells therein, precipitating the extracted DNA with isopropanol, and then washing with ethanol the precipitate obtained by centrifugation (refer to Current Protocols in Molecular Biology (Greene Publishing Associates and Wiley-Interscience), for example).

Such chromosomal DNA is used as a template, and PCR is carried out using the aforementioned DNA primers to obtain a portion of the gene of interest.

Subsequently, a DNA fragment encoding the N- and C-termini of the obtained partial gene can be obtained by the inverse PCR method (refer to Nucleic Acids Res. 16, 8186 (1988), for example). The nucleotide sequence of the above DNA fragment is determined. Thereafter, based on the nucleotide sequence of a portion presumably located upstream of the N-terminus of the enzyme and the nucleotide sequence of a portion presumably located downstream of the C-terminus thereof, DNA primers are prepared. Using such DNA primers, PCR is carried out with the obtained chromosomal DNA as a template to obtain a DNA fragment that contains the full-length amidase gene of interest.

Thereafter, the obtained DNA fragment that contains an amidase gene is allowed to bind to vector DNA using T4 DNA ligase, thereby obtaining a recombinant plasmid. Using this plasmid, the nucleotide sequence of the DNA fragment portion containing an amidase gene, which has been inserted into the vector, is analyzed to confirm the presence of nucleotides that encode the N-terminal amino acid sequence and internal amino acid sequence of an amidase enzyme. Moreover, a translation initiation site and a termination codon are confirmed to determine an open reading frame.

Host microorganisms are transformed with the thus obtained DNA or with a plasmid obtained by incorporation of the above DNA into a vector to obtain a transformant.

As a host and a vector, the host-vector system described in "*Kumikae DNA Jikken Shishin* (Recombinant DNA Experimental Guideline)" (edited by Science and Technology Agency, Research and Development Bureau, Life Sciences Division; revised on Mar. 22, 1996) can be used. Examples of a host used herein may include microorganisms belonging to genus *Escherichia, Pseudomonas, Flavobacterium, Bacillus, Serratia, Corynebacterium, Brevibacterium, Agrobacterium, Acetobacter, Gluconobacter, Lactobacillus, Streptococcus,* or *Streptomyces*.

As a vector, a plasmid, phage, or derivative thereof derived from microorganisms, which is capable of autonomously replicating in the aforementioned host, can be used. Among others, *Escherichia coli* is preferably used as a host microorganism, and a vector capable of autonomously replicating in such a microorganism is preferably used as a vector. Examples of such a vector may include pUC18, pUC19, pBR322, pACYC184, pSC101, pT7Blue, and pUCNT. Moreover, a vector, which is modified to have a strong constitutive promoter for increasing the production amount of enzyme, can also be used.

As an example of a transformant, *Escherichia coli* HB101 is transformed with a recombinant plasmid pHA002 obtained by incorporation of the DNA as obtained above into pUCNT (refer to WO94/03613) to obtain a transformant, *Escherichia coli* HB101 (pHA002).

The transformant *Escherichia coli* HB101 (pHA002) obtained by the present invention has been deposited with the National Institute of Advanced Industrial Science and Technology, an Independent Administrative Institution under the Ministry of Economy, Trade and Industry (under accession No. FERM BP-10193; a national deposition with the original deposition date of Jan. 22, 2004 has been transferred to an international deposition under the provisions of the Budapest Treaty).

The recombinant DNA technology used in the present invention is well known in the related field. For example, such a technology is described in Molecular Cloning 2nd Edition (Cold Spring Harbor Laboratory Press, 1989), and Current Protocols in Molecular Biology (Greene Publishing Associates and Wiley-Interscience).

The microorganism capable of producing the amidase of the present invention (*Arthrobacter* sp. KNK1101J, a mutant thereof, the aforementioned transformant, etc.) is cultured to produce the above enzyme at a high level. Thus, this technique can be used for production of D-amino acid.

Such a microorganism may be cultured in a common medium. As a medium used for the culture, a common medium that contains nutrients such as a carbon source, a nitrogen source, and inorganic salts, may be used. When a trace amount of organic nutrient such as vitamin or amino acid is added, preferred results can often be obtained. Examples of a carbon source, which is appropriately used, may include: carbohydrates such as glucose or sucrose; organic acids such as acetic acid; and alcohols. Examples of a nitrogen source used herein may include ammonium salts, ammonia water, ammonia gas, urea, yeast extract, peptone, and corn steep liquor. Examples of inorganic salts used herein may include phosphates, magnesium salts, potassium salts, sodium salts, calcium salts, iron salts, sulfates, and chlorides.

The culture may be carried out within a temperature range between 25° C. and 40° C. Such a temperature range is particularly preferably between 25° C. and 37° C. In addition, the culture may be carried out within a pH range between 4 and 8. Such a pH range is preferably between 5 and 7.5. Moreover, either a batch culture method or a continuous culture method may be applied.

Treatments for inducing the enzyme, such as addition of isopropyl-1-thio-β-D-galactoside (IPTG) or lactose, can also be carried out, as necessary.

When the amidase of the present invention is used for the stereoselective hydrolysis of an amino acid amide or amino acid ester, the culture as obtained above (a culture broth, cells of microorganisms) may be allowed to directly act thereon.

Otherwise, amidase may be isolated and purified from the culture before use.

EXAMPLES

Specific examples of the present invention will be given below. However, these examples are not intended to limit the scope of the present invention.

Example 1

Isolation and Purification of Amidase

The *Arthrobacter* sp. KNK1101J (accession No. FERM BP-10192) was inoculated into 6 ml of medium A (produced by mixing 10 g of meat extract, 5 g of yeast extract, 10 g of polypeptone, and 3 g of sodium chloride in deionized water to total 1 L in volume; pH 6.5 before sterilization), which had been sterilized in a test tube. Thereafter, the strain was subjected to an aerobic shaking culture at 30° C. for 24 hours. Thereafter, 2 ml of the culture broth was inoculated into 200 ml of medium A, which had been sterilized in a flask, and it was then subjected to an aerobic shaking culture at 30° C. for 48 hours. After completion of the culture, the cells were harvested by centrifugation, and they were then suspended in a 50 mM Tris-HCl buffer solution (pH 8.0) contained 1 mM dithiothreitol (DTT). The cells were then disrupted with ultrasonic wave, followed by centrifugation. Thereafter, ammonium sulfate was added to the supernatant, resulting in a 45% of the saturated solution, and the generated precipitate was then obtained by centrifugation. This fraction was dissolved in a 50 mM Tris-HCl buffer solution (pH 8.0) containing 1 mM DTT and dialyzed in the buffer solution. Thereafter, the resultant solution was applied to DEAE-TOYOPEAL (manufactured by Tosoh Corporation) to conduct column chromatography. After washing with the same above buffer solution, fractions with activity were collected by elution via concentration gradient from 0 M to 0.5 M sodium chloride with the above buffer solution. Ammonium sulfate was dissolved in such active fractions to a final concentration of 0.8 M, and the resultant was then applied to Phenyl-TOYOPEAL (manufactured by Tosoh Corporation) to conduct column chromatography. Thus, fractions were collected by elution via concentration gradient from 0.8 M to 0 M ammonium sulfate with a 50 mM Tris-HCl buffer solution (pH 8.0) that contained 1 mM DTT. The obtained active fractions were applied to MonoQ HR5/5 (manufactured by Amersham Pharmacia Biotech) to conduct column chromatography. After washing with a 50 mM Tris-HCl buffer solution (pH 8.0) that contained 1 mM DTT, fractions were collected by elution via concentration gradient from 0 M to 0.5 M sodium chloride with the above buffer solution. The obtained active fractions were concentrated with an ultrafiltration membrane (molecular weight cut off: 10,000). Thereafter, the concentrate was applied to Superdex 200 HR 10/30 (manufactured by Amersham Pharmacia Biotech) to conduct gel filtration via FPLC.

Fractions were then eluted with a 50 mM Tris-HCl buffer solution (pH 8.0) that contained 1 mM DTT and 0.15 M sodium chloride. The obtained active fractions were analyzed by SDS-polyacrylamide electrophoresis. As a result, amidase was detected in the form of a single band, and thus the purity of the purified enzyme could be confirmed.

Example 2

Hydrolysis of Amino Acid Amide with Amidase 0.1 ml of the purified amidase active fraction obtained in Example 1 was mixed with 0.1 ml of a 0.2 M Tris-HCl buffer solution (pH 8.5) that contained 0.5% of the compound shown in Table 2. The mixture was shaken at 30° C. for 15 hours. After completion of the reaction, solids were eliminated by centrifugation. The yield and optical purity of the generated amino acid were analyzed by high performance liquid chromatography. The results are shown in Table 2.

Conditions for Analysis by High Performance Liquid Chromatography

[Analysis of Yield of Amino Acid]

Column: COSMOSIL 5C18-AR (4.6 mm$\phi$×250 mm; manufactured by Nacalai Tesque, Inc.)

Eluent: 10 mM potassium phosphate buffer solution (pH 2)/acetonitrile=19/1

Flow rate: 0.5 ml/min.

Column temperature: 40° C.

Measurement wavelength: 210 nm

[Analysis of Optical Purity of Amino Acid]

Column: SUMICHIRAL OA-5000 (4.6 mm$\phi$×150 mm; manufactured by

Sumika Chemical Analysis Service, Ltd.)

Eluent: 2 mM copper sulfate/acetonitrile=85/15

Flow rate: 0.8 ml/min.

Column temperature: 40° C.

Measurement wavelength: 254 nm

TABLE 2

| | Generated amino acid | | |
|---|---|---|---|
| substrate | yield (mol %) | configuration | optical purity (% ee) |
| DL-phenylalanine amide hydrochloride | 47.2 | D | 98.5 |
| DL-leucine amide hydrochloride | 3.1 | D | 88.9 |

Example 3

Hydrolysis of Amino Acid Ester with Purified Amidase 0.1 ml of the purified amidase active fraction obtained in Example 1 was mixed with 0.1 ml of a 0.2 M 2-(N-morpholino)ethanosulfonic acid-NaOH buffer solution (pH 6.5) that contained a racemic phenylalanine ethyl ester with a concentration of 0.5%. The mixture was shaken at 30° C. for 15 hours. After completion of the reaction, solids were eliminated by centrifugation. The generated amino acid was analyzed by the same method as that described in Example 2. As a result, it was found that D-phenylalanine was obtained in a yield of 29.7 mol % and at an optical purity of 72.8% ee.

Example 4

Isolation of Amidase Gene

First, the cells were harvested by culturing the Arthrobacter sp. KNK1101J according to the same method as that described in Example 1 were dissolved in CTAB, chloroform and phenol, and were then treated therewith. Thereafter, the extracted DNA was precipitated with isopropanol, and the precipitate obtained by centrifugation was then washed with ethanol to prepare chromosomal DNA (refer to Current Protocols in Molecular Biology (Greene Publishing Associates and Wiley-Interscience)). Subsequently, the amino acid sequence of the amino terminus of the amidase purified in Example 1 was determined using a vapor-phase protein sequencer. Thereafter, lysyl endopeptidase was allowed to act on the amidase purified in Example 1 in the presence of 4 M urea. The generated polypeptide fragment was purified by reverse phase HPLC. Thereafter, the internal amino acid sequence of the amidase was determined by the same above method. Using a DNA primer (Primer-1; SEQ ID NO: 4 of the sequence listing) designed based on the N-terminal amino acid sequence and a DNA primer (Primer-2; SEQ ID NO: 5 of the sequence listing) designed based on the internal amino acid sequence, PCR was carried out with the previously obtained chromosomal DNA as a template. As a result, a portion of the amidase gene of interest (referred to as a partial gene) was obtained.

Subsequently, the following operations were carried out to obtain the full-length gene of interest. Based on the nucleotide sequences corresponding to each of the N-terminal portion and C-terminal portion of the enzyme in the aforementioned partial gene, DNA primers directed towards the external direction of the partial gene (Primer-3 shown in SEQ ID NO: 6 of the sequence listing; and Primer-4 shown in SEQ ID NO: 7 of the sequence listing) were synthesized. Using such primers, inverse PCR was carried out. As a template, DNA, which had been obtained by cyclization with T4 DNA ligase of a fragment obtained by decomposition of the previously obtained chromosomal DNA with restriction enzymes, SacII, PvuI, SalI, and XhoI, was used. As a result of the inverse PCR, a DNA fragment, which contained a gene portion located further outside of the previously obtained partial gene, was obtained. The nucleotide sequence of this DNA fragment was determined. Thereafter, there were prepared a DNA primer (Primer 5; SEQ ID NO: 8 of the sequence listing) having a sequence obtained by binding the restriction site of BamHI to the nucleotide sequence of a portion presumably located upstream of the N-terminus of the enzyme, and a DNA primer (Primer 6; SEQ ID NO: 9 of the sequence listing) having a sequence obtained by binding the restriction site of SacI to the nucleotide sequence of a portion presumably located downstream of the C-terminus of the enzyme. Using such DNA primers, DNA between the sequences was amplified by PCR to obtain a DNA fragment (SEQ ID NO: 2 of the sequence listing) that contained the full-length amidase gene. The nucleotide sequence of a portion of the obtained DNA fragment was analyzed, and as a result, it was confirmed that the full-length amidase gene (SEQ ID NO: 3 of the sequence listing) was contained therein.

Example 5

Production of Recombinant Plasmid that Contains Amidase Gene and Analysis of the Gene Using T4 DNA ligase, the DNA fragment that contained the full-length amidase gene obtained in Example 4 was ligated to a vector plasmid pT7Blue cleaved with the restriction enzyme EcoRV. As a result, a plasmid pHA001 that contained the amidase gene, as shown in the restriction map of FIG. 1, was obtained.

Figure 1:
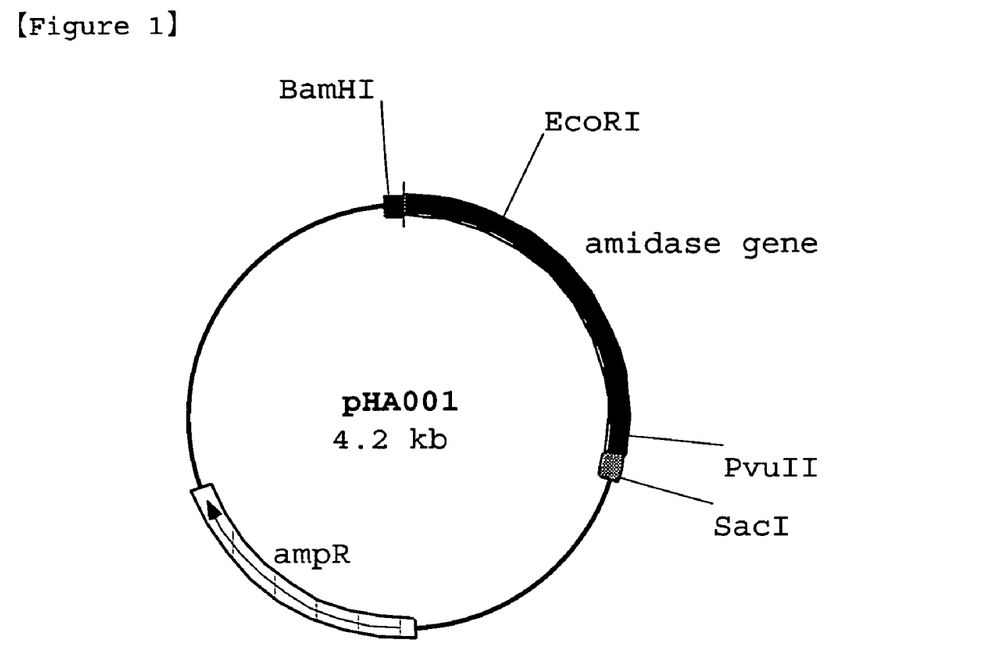
FIG. 1 is a view of a recombinant plasmid pHA001 comprising the amidase gene of the present invention.

Using the obtained plasmid pHA001, the nucleotide sequence of the DNA fragment obtained in Example 4 was analyzed. As a result, the presence of nucleotides encoding the N-terminal amino acid sequence and internal amino acid sequence determined with the purified amidase was confirmed. In addition, a translation initiation site and a termination codon were confirmed to determine an open reading frame. The nucleotide sequence of the thus obtained DNA fragment that contained the full-length amidase gene is shown in SEQ ID NO: 2 of the sequence listing. The nucleotide sequence of the open reading frame is shown in SEQ ID NO: 3 of the sequence listing. The amino acid sequence estimated from the nucleotide sequence is shown in SEQ ID NO: 1 of the sequence listing.

Example 6

Production of Recombinant Plasmid that Expresses Amidase Gene in High Volume Primers (Primer-7 shown in SEQ ID NO: 10 of the sequence listing; and Primer-8 shown in SEQ ID NO: 11 thereof) having sequences obtained by binding the restriction sites of NdeI and SacI to the N-terminal and C-terminal portions of the amidase gene obtained in Example 5, respectively, were used. DNA between them was amplified by PCR to obtain the DNA fragment of the open reading frame shown in SEQ ID NO: 3 of the sequence listing.

Figure 2:
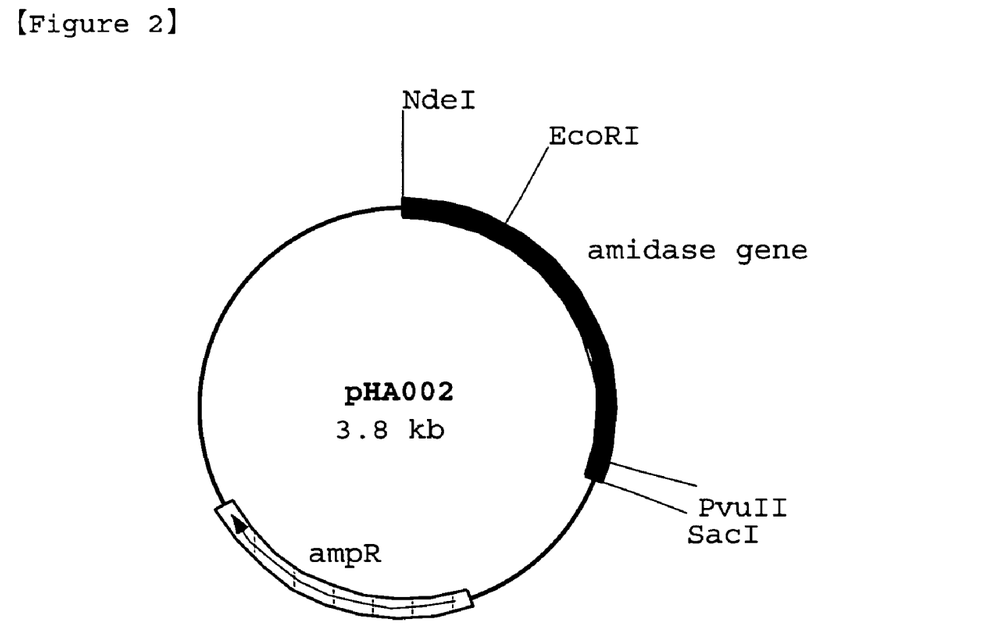
FIG. 2 is a view of a recombinant plasmid pHA002 comprising the amidase gene of the present invention.

The obtained DNA fragment was cleaved with the restriction enzymes NdeI and SacI. Using T4 DNA ligase, the cleaved portion was allowed to bind to a vector plasmid pUCNT (refer to WO94/03613), which had been cleaved with the same above enzymes. As a result, the pHA002 shown in the restriction map of FIG. 2, which had been designed to express a larger amount of amidase gene than pHA001 does, was obtained.

Example 7

Production of Transformant Using Recombinant DNA that Contains Amidase Gene

The plasmid pHA002 obtained in Example 6 was mixed with *Escherichia coli* HB101 competent cells to transform the cells. Thereafter, the cells were plated on agar medium B (produced by mixing 10 g of trypton, 5 g of yeast extract, 10 g of sodium chloride, 15 g of agar, and 100 mg of ampicillin, in 1 L of deionized water; pH 7.0 before sterilization; ampicillin was added after completion of the sterilization) to obtain a transformant, *Escherichia coli* HB101 (pHA002), which contained recombinant DNA that contained an amidase gene, in the form of a colony.

The obtained transformant colony was inoculated into 6 ml of medium C (produced by mixing 10 g of trypton, 5 g of yeast extract, 10 g of sodium chloride, and 100 mg ampicillin, in 1 L of deionized water; pH 7.0 before sterilization; ampicillin was added after completion of the sterilization), which had been sterilized in a test tube. Thereafter, the resultant was shaken at 37° C. for 24 hour for an aerobic culture. Thereafter, cells were harvested from the obtained culture broth by centrifugation, and it was then suspended in a 50 mM Tris-HCl buffer solution (pH 8.0) that contained 1 mM dithiothreitol (DTT). The cells were then disrupted with ultrasonic wave, and insoluble products derived from the cells were then eliminated by centrifugation to obtain an amidase solution of the transformant. 0.1 ml of the obtained enzyme solution was mixed with 0.1 ml of a 0.2 M Tris-HCl buffer solution (pH 8.5) that contained 50 mM D-phenylalanine amide hydrochloride. The obtained mixture was reacted at 30° C. for 15 hours. As a result, it was confirmed that D-phenylalanine was generated, and that the transformant had amidase activity.

It is to be noted that the obtained transformant, *Escherichia coli* HB101 (pHA002), has been deposited with the National Institute of Advanced Industrial Science and Technology, an Independent Administrative Institution under the Ministry of Economy, Trade and Industry (under accession No. FERM BP-10193; a national deposition with the original deposition date of Jan. 22, 2004 has been transferred to an international deposition under the provisions of the Budapest Treaty).

Example 8

Hydrolysis of Amino Acid Ester Using Recombinant Bacteria 0.1 ml of the culture broth of *Escherichia coli* HB101 (pHA002) obtained in Example 7 was mixed with 0.1 ml of a 0.2 M 2-(N-morpholino) ethanesulfonic acid-NaOH buffer solution (pH 6.5) that contained 10 of racemic phenylalanine ethyl ester. The obtained mixture was shaken at 30° C. for 15 hours. After completion of the reaction, solids were eliminated by centrifugation, and the generated amino acid was analyzed by the same method as that described in Example 2. As a result, it was found that D-phenylalanine was obtained at a yield of 34.7 mol % and an optical purity of 53.6% ee.

The invention claimed is:

1. An isolated polypeptide consisting of:
   (a) the amino acid sequence of SEQ ID NO: 1; or
   (b) an amino acid sequence resulting from substitution, insertion, deletion, and/or addition of one amino acid in the amino acid sequence of SEQ ID NO: 1, wherein the polypeptide has amidase activity.

2. The isolated polypeptide according to claim 1, wherein the polypeptide is derived from a microorganism belonging to the genus *Arthrobacter*.

3. The isolated polypeptide according to claim 2, wherein the microorganism is *Arthrobacter* sp. KNK1101J (FERM BP-10192).

4. An isolated DNA encoding the polypeptide of claim 1.

5. An isolated DNA consisting of:
   (a) the nucleotide sequence of SEQ ID NO: 3;
   (b) a nucleotide sequence that is capable of hybridizing, under stringent conditions, to the DNA having the nucleotide sequence that is complementary to the full-length nucleotide sequence of SEQ ID NO: 3, the stringent conditions being washing with an aqueous solution consisting of 1.5 mM trisodium citrate, 15 mM sodium chloride and 0.1% sodium dodecyl sulfate at 65° C. or
   (c) a nucleotide sequence resulting from substitution, insertion, deletion, and/or addition of one nucleotide in the nucleotide sequence of SEQ ID NO: 3,
   wherein the isolated DNA encodes a polypeptide having amidase activity.

6. A recombinant plasmid comprising the isolated DNA of claim 5 and a vector.

7. The recombinant plasmid according to claim 6, wherein the vector is pUC18, pUC19, pBR322, pACYC184, pSC101, pT7Blue, or pUCNT.

8. The recombinant plasmid according to claim 6, wherein the plasmid is pHA002.

9. A transformant, wherein the transformant is obtained by transformation of a host microorganism with the recombinant plasmid according to claim 6.

10. The transformant according to claim 9, wherein the host microorganism is *Escherichia coli*.

11. The transformant according to claim 9, wherein the transformant is *Escherichia coli* HB101 (pHA002) (FERM BP-10193).

12. An isolated microorganism, wherein the isolated microorganism produces the polypeptide according to claim 1 and belongs to genus *Arthrobacter*.

13. The isolated microorganism according to claim 12, the isolated microorganism being *Arthrobacter* sp. KNK1101J (FERM BP-10192) or a mutant thereof.

14. A method for producing an amidase, comprising culturing a microorganism that is able to produce the polypeptide according to claim 1,
accumulating said polypeptide in the culture, and
collecting said polypeptide.

15. The method according to claim 14, wherein the microorganism is a transformant obtained by transformation of a host microorganism with a recombinant plasmid, the recombinant plasmid comprising a DNA and a vector, wherein the DNA of the recombinant plasmid consists of
   (a) the nucleotide sequence of SEQ ID NO: 3;
   (b) a nucleotide sequence that is capable of hybridizing, under stringent conditions, to the DNA having the nucleotide sequence that is complementary to the full-length nucleotide sequence of SEQ ID NO: 3, the stringent conditions being washing with an aqueous solution consisting of 1.5 mM trisodium citrate, 15 mM sodium chloride and 0.1% sodium dodecyl sulfate at 65° C., or
   (c) the nucleotide sequence resulting from substitution, insertion, deletion, and/or addition of one nucleotide in a nucleotide sequence of SEQ ID NO: 3,
   wherein the DNA of the recombinant plasmid encodes a polypeptide having amidase activity.

16. The production method according to claim 14, wherein the microorganism belongs to the genus *Arthrobacter*.

17. A recombinant plasmid comprising the isolated DNA of claim 4 and a vector.

* * * * *

SEQUENCE LISTING

<160> NUMBER OF SEQ ID NOS: 11

<210> SEQ ID NO 1

<211> LENGTH: 388
<212> TYPE: PRT
<213> ORGANISM: Arthrobacter sp.

<400> SEQUENCE: 1

```
Met Ser Arg Leu Leu Arg Glu His Gly Ile Val Ile Gly Arg Leu Gln
1               5                   10                  15

Pro Gly Ser Leu Asn Thr Ile Ala Asp Val Ala Gly Val Arg Val Gly
            20                  25                  30

His Ser Thr Ile Met Arg Gly Ser Gly Pro Leu Ser Ile Gly His Gly
        35                  40                  45

Pro Val Arg Thr Gly Val Thr Ala Ile Ile Pro His Glu Gly Asp Ile
50                  55                  60

Trp Glu Glu Pro Arg Phe Ala Gly Val Phe Ser Leu Asn Gly Ser Gly
65                  70                  75                  80

Glu Trp Ser Gly Thr Ser Phe Val Arg Glu Thr Gly Cys Leu Tyr Gly
                85                  90                  95

Pro Ile Met Thr Thr Asn Ser His Ser Ile Gly Ser Val Arg Asn Ala
            100                 105                 110

Val Ile Lys Arg Glu Val Ala Arg Arg Gly Ser Leu Glu Arg Leu Pro
        115                 120                 125

Leu Val Gly Glu Thr Phe Asp Gly Leu Leu Asn Asp Ile Ser Gly Met
130                 135                 140

His Val Lys Asp Glu His Val Ala Glu Ala Ile Asp Ser Ala Ser Ala
145                 150                 155                 160

Asn Val Thr Glu Gly Asn Val Gly Gly Gly Thr Gly Asn Val Cys His
                165                 170                 175

Gly Phe Lys Gly Gly Ile Gly Ser Ala Ser Arg Val Leu Gln Leu Gly
            180                 185                 190

Glu Glu Thr Tyr Thr Leu Gly Val Leu Val Gln Ala Asn His Gly Leu
        195                 200                 205

Arg Asp Glu Phe Gln Val Thr Gly Val Pro Val Gly Arg Leu Ile Ser
210                 215                 220

Thr Asp Glu Ile Pro Leu Gly Pro Ser Gly Phe Asp Arg Arg Ser Ser
225                 230                 235                 240

Pro His Lys Asn Ser Ile Leu Val Val Ala Thr Asp Ala Pro Leu
                245                 250                 255

Leu Pro Gly Gln Leu Glu Arg Val Ala His Arg Ser Thr Leu Gly Ile
            260                 265                 270

Ala Arg Asn Gly Ala Tyr Ala His Asn Leu Ser Gly Asp Leu Ala Leu
        275                 280                 285

Ala Phe Ser Thr Cys Pro Gln Pro Val Ser Gly Tyr Asp Phe Gly Val
290                 295                 300

Asp Thr Ser Pro Gly Thr Ile Arg Ala Leu Pro Asn Ala Ala Thr Ala
305                 310                 315                 320

Gly Leu Phe Glu Ala Ala Val Glu Ala Thr Glu Glu Ala Ile Val Ser
                325                 330                 335

Ala Leu Val His Ala Asp Thr Cys Thr Gly Ile Asp Asp Arg Val Ala
            340                 345                 350

Tyr Gly Leu Glu Ala Ala Arg Leu Ala Arg Ser Ile Ser Glu Tyr Arg
        355                 360                 365

Gly Thr Gln Leu Tyr Pro Glu Lys Val Ser Asp Ser His Leu Glu Arg
370                 375                 380

Arg Ser Gln Pro
```

```
<210> SEQ ID NO 2
<211> LENGTH: 1290
<212> TYPE: DNA
<213> ORGANISM: Arthrobacter sp.
<220> FEATURE:
<221> NAME/KEY: CDS
<222> LOCATION: (53)..(1219)
<223> OTHER INFORMATION: sequence coding for amidase

<400> SEQUENCE: 2
```

| | | | | | | | | | | | | | | | |
|---|---|---|---|---|---|---|---|---|---|---|---|---|---|---|---|
| agcgcgtcgt | ggactgggtg | cagaaataca | caggcgagcc | cgaggacgaa | aa | atg | agc | | | | | | | | 58 |
| | | | | | | Met | Ser | | | | | | | | |
| | | | | | | 1 | | | | | | | | | |

| cgt | ctg | ctc | cgt | gag | cac | gga | atc | gtc | atc | ggt | cgt | ctc | caa | ccg | ggt | 106 |
|---|---|---|---|---|---|---|---|---|---|---|---|---|---|---|---|---|
| Arg | Leu | Leu | Arg | Glu | His | Gly | Ile | Val | Ile | Gly | Arg | Leu | Gln | Pro | Gly | |
| | 5 | | | | | 10 | | | | | 15 | | | | | |

| tct | ctg | aac | acc | att | gca | gac | gtc | gca | ggc | gtt | cgc | gta | ggc | cat | tca | 154 |
|---|---|---|---|---|---|---|---|---|---|---|---|---|---|---|---|---|
| Ser | Leu | Asn | Thr | Ile | Ala | Asp | Val | Ala | Gly | Val | Arg | Val | Gly | His | Ser | |
| 20 | | | | | 25 | | | | | 30 | | | | | | |

| aca | atc | atg | cgc | ggt | tct | ggg | ccc | ctg | tcc | atc | ggc | cat | ggc | cca | gtt | 202 |
|---|---|---|---|---|---|---|---|---|---|---|---|---|---|---|---|---|
| Thr | Ile | Met | Arg | Gly | Ser | Gly | Pro | Leu | Ser | Ile | Gly | His | Gly | Pro | Val | |
| 35 | | | | 40 | | | | | 45 | | | | | 50 | | |

| cgc | aca | ggg | gta | aca | gcc | atc | atc | cct | cac | gaa | gga | gac | atc | tgg | gag | 250 |
|---|---|---|---|---|---|---|---|---|---|---|---|---|---|---|---|---|
| Arg | Thr | Gly | Val | Thr | Ala | Ile | Ile | Pro | His | Glu | Gly | Asp | Ile | Trp | Glu | |
| | | | | 55 | | | | | 60 | | | | | 65 | | |

| gag | cca | cgg | ttc | gcc | ggc | gtc | ttc | tcc | ctg | aat | ggc | agc | ggt | gaa | tgg | 298 |
|---|---|---|---|---|---|---|---|---|---|---|---|---|---|---|---|---|
| Glu | Pro | Arg | Phe | Ala | Gly | Val | Phe | Ser | Leu | Asn | Gly | Ser | Gly | Glu | Trp | |
| | | 70 | | | | | 75 | | | | | 80 | | | | |

| agc | gga | acc | tcg | ttc | gtc | agg | gag | acc | ggg | tgt | ctt | tat | ggc | cct | atc | 346 |
|---|---|---|---|---|---|---|---|---|---|---|---|---|---|---|---|---|
| Ser | Gly | Thr | Ser | Phe | Val | Arg | Glu | Thr | Gly | Cys | Leu | Tyr | Gly | Pro | Ile | |
| | 85 | | | | | 90 | | | | | 95 | | | | | |

| atg | acg | acg | aat | tcg | cac | agc | att | gga | tcg | gtc | agg | aac | gcc | gtc | atc | 394 |
|---|---|---|---|---|---|---|---|---|---|---|---|---|---|---|---|---|
| Met | Thr | Thr | Asn | Ser | His | Ser | Ile | Gly | Ser | Val | Arg | Asn | Ala | Val | Ile | |
| 100 | | | | | 105 | | | | | 110 | | | | | | |

| aag | cgt | gaa | gta | gcc | cgg | cgg | gga | agc | ctg | gag | agg | ctc | cct | ctc | gtg | 442 |
|---|---|---|---|---|---|---|---|---|---|---|---|---|---|---|---|---|
| Lys | Arg | Glu | Val | Ala | Arg | Arg | Gly | Ser | Leu | Glu | Arg | Leu | Pro | Leu | Val | |
| 115 | | | | 120 | | | | | 125 | | | | | 130 | | |

| gga | gaa | acc | ttt | gat | ggc | cta | ctc | aat | gac | atc | agc | ggc | atg | cac | gtc | 490 |
|---|---|---|---|---|---|---|---|---|---|---|---|---|---|---|---|---|
| Gly | Glu | Thr | Phe | Asp | Gly | Leu | Leu | Asn | Asp | Ile | Ser | Gly | Met | His | Val | |
| | | | | 135 | | | | | 140 | | | | | 145 | | |

| aag | gac | gaa | cac | gtg | gcc | gag | gcc | atc | gac | tcc | gcc | tcc | gca | aat | gtt | 538 |
|---|---|---|---|---|---|---|---|---|---|---|---|---|---|---|---|---|
| Lys | Asp | Glu | His | Val | Ala | Glu | Ala | Ile | Asp | Ser | Ala | Ser | Ala | Asn | Val | |
| | | | 150 | | | | | 155 | | | | | 160 | | | |

| acc | gaa | ggc | aat | gtt | ggc | ggt | ggg | acc | gga | aat | gtt | tgt | cac | ggt | ttc | 586 |
|---|---|---|---|---|---|---|---|---|---|---|---|---|---|---|---|---|
| Thr | Glu | Gly | Asn | Val | Gly | Gly | Gly | Thr | Gly | Asn | Val | Cys | His | Gly | Phe | |
| | | 165 | | | | | 170 | | | | | 175 | | | | |

| aaa | ggc | ggt | att | gga | agt | gcc | tcg | cgc | gtg | ttg | caa | ttg | ggc | gag | gaa | 634 |
|---|---|---|---|---|---|---|---|---|---|---|---|---|---|---|---|---|
| Lys | Gly | Gly | Ile | Gly | Ser | Ala | Ser | Arg | Val | Leu | Gln | Leu | Gly | Glu | Glu | |
| | 180 | | | | | 185 | | | | | 190 | | | | | |

| acc | tac | act | ttg | ggg | gtt | ctc | gtc | caa | gcc | aac | cac | ggc | ctt | cgt | gac | 682 |
|---|---|---|---|---|---|---|---|---|---|---|---|---|---|---|---|---|
| Thr | Tyr | Thr | Leu | Gly | Val | Leu | Val | Gln | Ala | Asn | His | Gly | Leu | Arg | Asp | |
| 195 | | | | 200 | | | | | 205 | | | | | 210 | | |

| gaa | ttt | cag | gtg | acg | gga | gta | ccc | gtg | gga | agg | ctc | ata | tct | acg | gac | 730 |
|---|---|---|---|---|---|---|---|---|---|---|---|---|---|---|---|---|
| Glu | Phe | Gln | Val | Thr | Gly | Val | Pro | Val | Gly | Arg | Leu | Ile | Ser | Thr | Asp | |
| | | | | 215 | | | | | 220 | | | | | 225 | | |

| gag | atc | ccc | ttg | ggg | cct | tca | ggt | ttt | gat | cga | agg | tct | tca | cca | cac | 778 |
|---|---|---|---|---|---|---|---|---|---|---|---|---|---|---|---|---|
| Glu | Ile | Pro | Leu | Gly | Pro | Ser | Gly | Phe | Asp | Arg | Arg | Ser | Ser | Pro | His | |
| | | | 230 | | | | | 235 | | | | | 240 | | | |

| aaa | aac | agt | att | ctt | gtc | gtc | gtg | gca | acc | gac | gcg | cct | cta | cta | ccg | 826 |

-continued

```
                Lys Asn Ser Ile Leu Val Val Ala Thr Asp Ala Pro Leu Leu Pro
                        245                 250                 255 ggc caa ctg gaa cgc gtt gct cac cgt tct acc cta ggc att gcc cgt       874
Gly Gln Leu Glu Arg Val Ala His Arg Ser Thr Leu Gly Ile Ala Arg
    260                 265                 270 aat ggt gcc tac gcg cac aat ctc agc ggc gac ctt gca ctt gcg ttc       922
Asn Gly Ala Tyr Ala His Asn Leu Ser Gly Asp Leu Ala Leu Ala Phe
275                 280                 285                 290 tcc acc tgc ccg cag cct gta agc ggt tac gat ttc gga gtg gat aca       970
Ser Thr Cys Pro Gln Pro Val Ser Gly Tyr Asp Phe Gly Val Asp Thr
                295                 300                 305 agt cct ggg acc att cgc gcc ctg ccc aac gcc gca acg gct ggc ctc      1018
Ser Pro Gly Thr Ile Arg Ala Leu Pro Asn Ala Ala Thr Ala Gly Leu
            310                 315                 320 ttc gag gcg gcc gtt gag gcc act gag gaa gcg att gtt tcc gcg ctt      1066
Phe Glu Ala Ala Val Glu Ala Thr Glu Glu Ala Ile Val Ser Ala Leu
        325                 330                 335 gtc cac gcc gac acc tgc acc ggg atc gat gac agg gtt gcc tat ggg      1114
Val His Ala Asp Thr Cys Thr Gly Ile Asp Asp Arg Val Ala Tyr Gly
    340                 345                 350 ttg gag gcg gct cga ctt gct cgt tca att tcg gaa tat cga ggc acc      1162
Leu Glu Ala Ala Arg Leu Ala Arg Ser Ile Ser Glu Tyr Arg Gly Thr
355                 360                 365                 370 cag ctg tat ccg gag aaa gtg tcg gat tcc cat ctt gaa cga agg agc      1210
Gln Leu Tyr Pro Glu Lys Val Ser Asp Ser His Leu Glu Arg Arg Ser
                375                 380                 385 cag ccg tga ccgccgcgca gccaagccaa gcaccacccc gggcaaaggc              1259
Gln Pro cgggaaacgg tccaacctaa cacgcaacga t                                   1290
```

<210> SEQ ID NO 3
<211> LENGTH: 1167
<212> TYPE: DNA
<213> ORGANISM: Arthrobacter sp.
<220> FEATURE:
<221> NAME/KEY: CDS
<222> LOCATION: (1)..(1167)
<223> OTHER INFORMATION: sequence coding for amidase

<400> SEQUENCE: 3

```
atg agc cgt ctg ctc cgt gag cac gga atc gtc atc ggt cgt ctc caa        48
Met Ser Arg Leu Leu Arg Glu His Gly Ile Val Ile Gly Arg Leu Gln
1               5                  10                  15 ccg ggt tct ctg aac acc att gca gac gtc gca ggc gtt cgc gta ggc        96
Pro Gly Ser Leu Asn Thr Ile Ala Asp Val Ala Gly Val Arg Val Gly
                20                  25                  30 cat tca aca atc atg cgc ggt tct ggg ccc ctg tcc atc ggc cat ggc       144
His Ser Thr Ile Met Arg Gly Ser Gly Pro Leu Ser Ile Gly His Gly
            35                  40                  45 cca gtt cgc aca ggg gta aca gcc atc atc cct cac gaa gga gac atc       192
Pro Val Arg Thr Gly Val Thr Ala Ile Ile Pro His Glu Gly Asp Ile
        50                  55                  60 tgg gag gag cca cgg ttc gcc ggc gtc ttc tcc ctg aat ggc agc ggt       240
Trp Glu Glu Pro Arg Phe Ala Gly Val Phe Ser Leu Asn Gly Ser Gly
65                  70                  75                  80 gaa tgg agc gga acc tcg ttc gtc agg gag acc ggg tgt ctt tat ggc       288
Glu Trp Ser Gly Thr Ser Phe Val Arg Glu Thr Gly Cys Leu Tyr Gly
                85                  90                  95 cct atc atg acg acg aat tcg cac agc att gga tcg gtc agg aac gcc       336
Pro Ile Met Thr Thr Asn Ser His Ser Ile Gly Ser Val Arg Asn Ala
            100                 105                 110
```

```
gtc atc aag cgt gaa gta gcc cgg cgg gga agc ctg gag agg ctc cct    384
Val Ile Lys Arg Glu Val Ala Arg Arg Gly Ser Leu Glu Arg Leu Pro
        115                 120                 125 ctc gtg gga gaa acc ttt gat ggc cta ctc aat gac atc agc ggc atg    432
Leu Val Gly Glu Thr Phe Asp Gly Leu Leu Asn Asp Ile Ser Gly Met
130                 135                 140 cac gtc aag gac gaa cac gtg gcc gag gcc atc gac tcc gcc tcc gca    480
His Val Lys Asp Glu His Val Ala Glu Ala Ile Asp Ser Ala Ser Ala
145                 150                 155                 160 aat gtt acc gaa ggc aat gtt ggc ggt ggg acc gga aat gtt tgt cac    528
Asn Val Thr Glu Gly Asn Val Gly Gly Gly Thr Gly Asn Val Cys His
                165                 170                 175 ggt ttc aaa ggc ggt att gga agt gcc tcg cgc gtg ttg caa ttg ggc    576
Gly Phe Lys Gly Gly Ile Gly Ser Ala Ser Arg Val Leu Gln Leu Gly
            180                 185                 190 gag gaa acc tac act ttg ggg gtt ctc gtc caa gcc aac cac ggc ctt    624
Glu Glu Thr Tyr Thr Leu Gly Val Leu Val Gln Ala Asn His Gly Leu
        195                 200                 205 cgt gac gaa ttt cag gtg acg gga gta ccc gtg gga agg ctc ata tct    672
Arg Asp Glu Phe Gln Val Thr Gly Val Pro Val Gly Arg Leu Ile Ser
210                 215                 220 acg gac gag atc ccc ttg ggg cct tca ggt ttt gat cga agg tct tca    720
Thr Asp Glu Ile Pro Leu Gly Pro Ser Gly Phe Asp Arg Arg Ser Ser
225                 230                 235                 240 cca cac aaa aac agt att ctt gtc gtc gtg gca acc gac gcg cct cta    768
Pro His Lys Asn Ser Ile Leu Val Val Val Ala Thr Asp Ala Pro Leu
                245                 250                 255 cta ccg ggc caa ctg gaa cgc gtt gct cac cgt tct acc cta ggc att    816
Leu Pro Gly Gln Leu Glu Arg Val Ala His Arg Ser Thr Leu Gly Ile
            260                 265                 270 gcc cgt aat ggt gcc tac gcg cac aat ctc agc ggc gac ctt gca ctt    864
Ala Arg Asn Gly Ala Tyr Ala His Asn Leu Ser Gly Asp Leu Ala Leu
        275                 280                 285 gcg ttc tcc acc tgc ccg cag cct gta agc ggt tac gat ttc gga gtg    912
Ala Phe Ser Thr Cys Pro Gln Pro Val Ser Gly Tyr Asp Phe Gly Val
290                 295                 300 gat aca agt cct ggg acc att cgc gcc ctg ccc aac gcc gca acg gct    960
Asp Thr Ser Pro Gly Thr Ile Arg Ala Leu Pro Asn Ala Ala Thr Ala
305                 310                 315                 320 ggc ctc ttc gag gcg gcc gtt gag gcc act gag gaa gcg att gtt tcc   1008
Gly Leu Phe Glu Ala Ala Val Glu Ala Thr Glu Glu Ala Ile Val Ser
                325                 330                 335 gcg ctt gtc cac gcc gac acc tgc acc ggg atc gat gac agg gtt gcc   1056
Ala Leu Val His Ala Asp Thr Cys Thr Gly Ile Asp Asp Arg Val Ala
            340                 345                 350 tat ggg ttg gag gcg gct cga ctt gct cgt tca att tcg gaa tat cga   1104
Tyr Gly Leu Glu Ala Ala Arg Leu Ala Arg Ser Ile Ser Glu Tyr Arg
        355                 360                 365 ggc acc cag ctg tat ccg gag aaa gtg tcg gat tcc cat ctt gaa cga   1152
Gly Thr Gln Leu Tyr Pro Glu Lys Val Ser Asp Ser His Leu Glu Arg
370                 375                 380 agg agc cag ccg tga                                               1167
Arg Ser Gln Pro
385

<210> SEQ ID NO 4
<211> LENGTH: 16
<212> TYPE: DNA
<213> ORGANISM: Artificial Sequence
<220> FEATURE:
```

-continued

```
<223> OTHER INFORMATION: Description of Artificial Sequence: primer-1
<220> FEATURE:
<221> NAME/KEY: misc_feature
<222> LOCATION: (2)..(2)
<223> OTHER INFORMATION: n represents a, t, g or c
<220> FEATURE:
<221> NAME/KEY: misc_feature
<222> LOCATION: (11)..(11)
<223> OTHER INFORMATION: n represents a, t, g or c

<400> SEQUENCE: 4
gngarcaygg nathgt                                                  16

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: primer-2
<220> FEATURE:
<221> NAME/KEY: misc_feature
<222> LOCATION: (6)..(6)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 5
gtrtangtyt cytcncc                                                 17

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer-3

<400> SEQUENCE: 6
tgccattcag ggagaagac                                               19

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: primer-4

<400> SEQUENCE: 7
cacgtcaagg acgaacac                                                18

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: primer-5

<400> SEQUENCE: 8
taattaggat ccagcgcgtc gtggactg                                     28

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: primer-6

<400> SEQUENCE: 9
```

```
-continued ataaccggag ctcatcgttg cgtgttaggt t                                          31

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: primer-7

<400> SEQUENCE: 10
tcctgctcat atgagccgtc tgctccgt                                              28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: primer-8

<400> SEQUENCE: 11
attctatgag ctcacggctg gctccttcg                                             29
```